(12) United States Patent
Lee et al.

(10) Patent No.: US 11,452,784 B2
(45) Date of Patent: Sep. 27, 2022

(54) SIZE-VARYING BUBBLE COMPLEX AND METHOD OF PREPARING THE SAME

(71) Applicant: SOGANG UNIVERSITY RESEARCH FOUNDATION, Seoul (KR)

(72) Inventors: Seung-Yop Lee, Seoul (KR); Se-Yun Jeong, Yongin-si (KR); Han-Bok Seo, Seoul (KR); Eun Ae Park, Geoje-si (KR); Won-Joong Kim, Buan-gun (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 80 days.

(21) Appl. No.: 16/876,606

(22) Filed: May 18, 2020

(65) Prior Publication Data
US 2020/0384133 A1   Dec. 10, 2020

(30) Foreign Application Priority Data
Jun. 4, 2019   (KR) .................. 10-2019-0065979

(51) Int. Cl.
*A61B 8/00* (2006.01)
*A61K 49/22* (2006.01)
*A61K 49/00* (2006.01)

(52) U.S. Cl.
CPC ........ *A61K 49/223* (2013.01); *A61K 49/0002* (2013.01)

(58) Field of Classification Search
CPC .................. A61K 49/223; A61K 49/0002
See application file for complete search history.

(56) References Cited

U.S. PATENT DOCUMENTS 10,577,554 B2 * 3/2020 Kheir ................. A61K 47/6925

FOREIGN PATENT DOCUMENTS

KR   10-2015-0010908 A   1/2015

OTHER PUBLICATIONS

Hettiarachchi et al. (J. Colloid Interface Sci. 2010, 344, 521-527).*

* cited by examiner

*Primary Examiner* — Michael G. Hartley
*Assistant Examiner* — Melissa J Perreira
(74) *Attorney, Agent, or Firm* — Goldilocks Zone IP Law (57) ABSTRACT

Proposed is to provide a size-varying bubble complex and a method of preparing the same. More specifically, the size-varying bubble complex and the method of preparing the same are proposed, wherein the bubble complex is capable of being repeatedly varied in size by changing phases of perfluorocarbon by external stimuli, by including a shell that encapsulates a core made of the perfluorocarbon and protects the core by expanding and contracting together when the core expands and contracts.

2 Claims, 5 Drawing Sheets
(3 of 5 Drawing Sheet(s) Filed in Color)

SIZE-VARYING BUBBLE COMPLEX AND METHOD OF PREPARING THE SAME

CROSS REFERENCE TO RELATED APPLICATION

The present application claims priority to Korean Patent Application No. 10-2019-0065979, filed Jun. 4, 2019, the entire contents of which is incorporated herein for all purposes by this reference.

BACKGROUND OF THE INVENTION

Field of the Invention

The present invention relates to a size-varying bubble complex and a method of preparing the same. More specifically, the present invention relates to a size-varying bubble complex and a method of preparing the same, wherein the bubble complex is capable of being repeatedly varied in size by changing phases of the perfluorocarbon by external stimuli, by including a shell that encapsulates a core made of perfluorocarbon and protects the core by expanding and contracting together when the core expands and contracts.

Description of the Related Art

Recently, with development of micro-nano-level preparing technology, micro-manipulation technology capable of precisely and selectively driving small objects has been studied. An example of the micro-manipulation technology may include an oscillating bubble technique that transports objects around the bubble or manipulates movement thereof by utilizing the characteristics of the periodic size-variation of microbubbles caused by external stimuli. One example of a bubble that periodically varies in size to external stimuli may be an air bubble as described in the following paper.
<Related Paper>
Jian Feng, and Sung Kwon Cho, "Two-dimensionally steering microswimmer propelled by oscillating bubbles", in International Conference on Micro Electro Mechanical Systems (MEMS 2014)

However, in the case of a commonly used air bubble, there is a problem that a large propulsive force may not be provided due to a small change rate to external stimuli. On the other hand, as is for the air bubble, there is a problem that a perfluorocarbon bubble used in vibrating bubble technology has a large size-varying characteristic during phase change but has low persistence and repeatability. Accordingly, the perfluorocarbon bubble is used for an engine inside an actuator in which perfluorocarbon is used as a consumable or is used only to an extent to play a role as a trigger for micro-bullets used on a one-off basis.

The foregoing is intended merely to aid in the understanding of the background of the present invention, and is not intended to mean that the present invention falls within the purview of the related art that is already known to those skilled in the art.

SUMMARY OF THE INVENTION

Accordingly, the present invention has been made keeping in mind the above problems occurring in the related art, and an objective of the present invention is to provide a size-varying bubble complex, which is capable of being repeatedly varied in size by changing phases of perfluorocarbon by external stimuli, by including a shell that encapsulates a core made of the perfluorocarbon and protects the core by expanding and contracting together when the core expands and contracts.

In addition, it is an objective of the present invention to provide the bubble complex having various shapes and sizes.

In addition, it is an objective of the present invention to provide the bubble complex that can position perfluorocarbon at the center thereof by including a coating layer positioned between the core and the shell and made of alginate.

In addition, it is an objective of the present invention to provide a method of preparing the bubble complex wherein the perfluorocarbon, whose outer surface is encapsulated with the elastic material liquid solution, can be prevented from adhering to a wall surface of a container in a preparing process, while positioning the perfluorocarbon at a center of the bubble complex, by applying centrifugal force to the supporting liquid solution and then curing the supporting liquid solution, after injecting the perfluorocarbon, whose outer surface is encapsulated with the elastic material liquid solution into the supporting liquid solution having a density similar to the elastic material liquid solution but having a high viscosity.

In addition, it is an objective of the present invention to provide a method of preparing the bubble complex wherein, by using corn syrup, a thin-thickness coating layer can be provided through a reaction that occurred as the alginate liquid solution is brought into contact with the calcium chloride solution as the corn syrup gradually dissolves.

In order to achieve the above objective, the present invention is implemented by embodiments having following configuration.

According to an embodiment of the present invention, there may be provided a size-varying bubble complex according to the present invention, the bubble complex including: a core made of the perfluorocarbon; and a shell encapsulating the core and protecting the core by expanding and contracting together when the core expands and contracts, wherein the bubble complex is capable of being repeatedly varied in size by changing phases of the perfluorocarbon by external stimuli.

According to another embodiment of the present invention, in the bubble complex according to the present invention, the shell may be made of an elastic material.

According to still another embodiment of the present invention, in the bubble complex according to the present invention, the shell may be made of PDMS.

According to still another embodiment of the present invention, in the bubble complex according to the present invention, the bubble complex may change phases of the perfluorocarbon by heating or by applying ultrasonic waves or a laser.

According to still another embodiment of the present invention, there may be provided a size-varying bubble complex according to the present invention, the bubble complex including: a core made of perfluorocarbon; a coating layer encapsulating the core and made of alginate; and a shell encapsulating the coating layer and protecting the core by expanding and contracting together when the core expands and contracts, wherein the bubble complex is capable of being repeatedly varied in size by changing phases of the perfluorocarbon by external stimuli.

According to still another embodiment of the present invention, in the bubble complex according to the present invention, the coating layer may be provided with a thickness of 0.01 to 0.1 mm and may be broken in a first expansion process of the core and thus may not affect the repeated size-variation of the bubble complex.

According to still another embodiment of the present invention, there may be provided a preparing method of a bubble complex according to the present invention, the method including: injecting perfluorocarbon into an elastic material liquid solution; obtaining the perfluorocarbon whose outer surface is encapsulated with the elastic material liquid solution by absorbing the perfluorocarbon injected into the elastic material liquid solution; re-injecting by injecting the perfluorocarbon whose outer surface is encapsulated with the elastic material liquid solution into a supporting liquid solution; and curing the bubble complex provided with the core made of the perfluorocarbon and a shell encapsulating the core and made of an elastic material by rotating a container containing the supporting liquid solution to apply centrifugal force to the supporting liquid solution, and simultaneously naturally curing the supporting liquid solution.

According to still another embodiment of the present invention, in the method according to the present invention, the supporting liquid solution may have a density similar to the elastic material liquid solution but have high viscosity and may be cured for 20 to 30 hours at a temperature of 20 to 30° C.

According to still another embodiment of the present invention, in the method according to the present invention, a PDMS liquid solution may be used as the elastic material liquid solution, and the supporting liquid solution may have a density less or greater than the elastic material liquid solution within a range of 10%, and a viscosity of two to four times of the elastic material liquid solution According to still another embodiment of the present invention, there may be provided a preparing method of a bubble complex according to the present invention, the method including: a first injection step of injecting perfluorocarbon into an alginate liquid solution; a first obtaining step of obtaining perfluorocarbon whose outer surface is encapsulated with the alginate liquid solution by absorbing perfluorocarbon injected into the alginate liquid solution; a second injection step of injecting perfluorocarbon whose outer surface is encapsulated with the alginate liquid solution into corn syrup; a second obtaining step of obtaining perfluorocarbon coated in turn with the alginate liquid solution and corn syrup by absorbing perfluorocarbon injected into the corn syrup; a coating step of providing a PFC-coating layer complex, which has the core made of perfluorocarbon and a coating layer encapsulating the core and made of alginate, the PFC-coating layer complex provided through a reaction that occurs as the alginate liquid solution is brought into contact with the calcium chloride solution as the corn syrup gradually dissolves by injecting the perfluorocarbon coated in turn with the alginate liquid solution and corn syrup into calcium chloride solution to react to each other; a third obtaining step of obtaining the PFC-coating layer complex whose outer surface is encapsulated with the elastic material liquid solution by absorbing the PFC-coating layer complex injected into the elastic material liquid solution; a fourth injection step of injecting the PFC-coating layer complex whose outer surface is encapsulated with the elastic material liquid solution; and a curing step of providing the bubble complex, provided with the core made of perfluorocarbon and a coating layer, which encapsulates the core and is made of the alginate, and a shell which encapsulates the coating layer and is made of the elastic material, by rotating a container containing the supporting liquid solution to apply centrifugal force to the supporting liquid solution and simultaneously naturally curing the supporting liquid solution.

According to still another embodiment of the present invention, in the method according to the present invention, the PDMS liquid solution may be used as the elastic material liquid solution, and epoxy resin may be used as the supporting liquid solution.

As described above, the present invention can obtain the following effects by the present embodiments.

The present invention has an effect wherein the bubble complex is capable of being repeatedly varied in size by changing phases of perfluorocarbon by external stimuli, by including a shell that encapsulates a core made of the perfluorocarbon and protects the core by expanding and contracting together when the core expands and contracts.

In addition, the present invention has an effect wherein the bubble complex can be provided having various shapes and sizes.

In addition, the present invention has an effect wherein perfluorocarbon can be positioned at the center by including a coating layer positioned between the core and the shell and made of alginate.

In addition, the present invention has an effect wherein the perfluorocarbon, whose outer surface is encapsulated with the elastic material liquid solution, can be prevented from adhering to a wall surface of a container in a preparing process, while positioning perfluorocarbon at a center of the bubble complex, by applying centrifugal force to the supporting liquid solution and then curing the supporting liquid solution, after injecting the perfluorocarbon, whose outer surface is encapsulated with the elastic material liquid solution into the supporting liquid solution having a density similar to the elastic material liquid solution but having a high viscosity.

In addition, the present invention has an effect wherein, by using corn syrup, a thin-thickness coating layer can be provided through a reaction that occurred as the alginate liquid solution is brought into contact with the calcium chloride solution as the corn syrup gradually dissolves.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objectives, features, and other advantages of the present invention will be more clearly understood from the following detailed description when taken in conjunction with the accompanying drawings, in which.

DETAILED DESCRIPTION OF THE INVENTION

Hereinafter, a size-varying bubble complex and a method of preparing the same according to the present invention will be described with reference to the accompanying drawings. Unless otherwise specified, all terms in this specification are the same as the general meaning of the terms understood by a person skilled in the art to which the present invention belongs, and when there is a conflict with the meaning of a term used in the present specification, the meaning of the term follows the definition used in the specification. In addition, detailed descriptions of well-known functions and configurations that may unnecessarily obfuscate the subject matter of the present invention are omitted. Throughout the specification, when a part "includes" a certain component, it means that the component does not exclude, but may further include, other components unless otherwise stated.

Describing the size-varying bubble complex according to an embodiment of the present invention with reference to FIGS. 1 to 5, the bubble complex may include a core 1 made of perfluorocarbon and a shell 2 encapsulating the core 1 and protecting the core by expanding and contracting together when the core expands and contracts, wherein the bubble complex is capable of being repeatedly varied in size by changing phases of the perfluorocarbon by external stimuli.

The core 1 is made of the perfluorocarbon, and perfluorocarbon in a liquid or gaseous state may be used.

Figure 1:
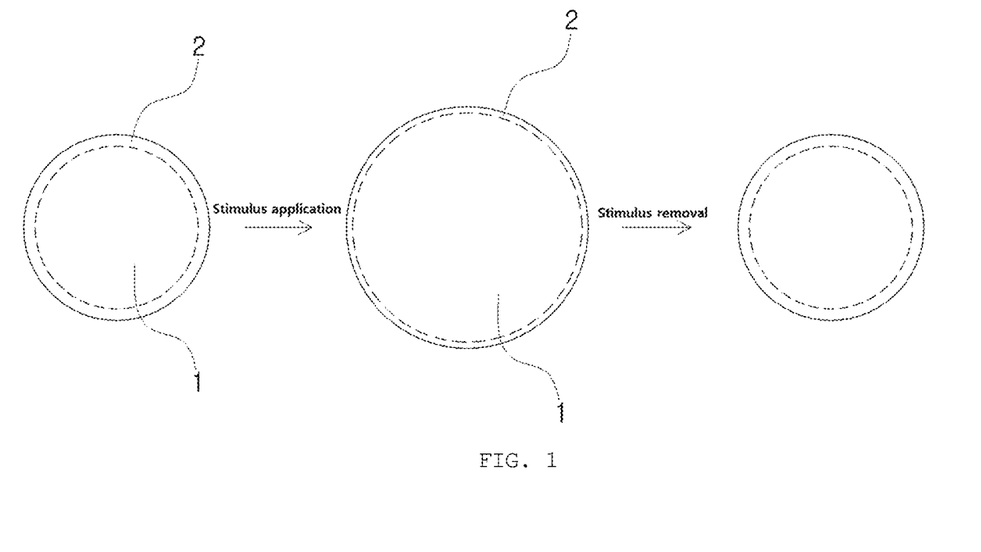
FIG. 1 shows reference views illustrating a size-varying process of a bubble complex according to an embodiment of the present invention.

The shell 2 encapsulates the core 1 and is configured to protect the core by expanding and contracting together when the core expands and contracts, and may be made of an elastic material, and for example, PDMS may be used. As previously seen, bubbles or liquid droplets of the perfluorocarbon have a large size-varying characteristic during phase change but have a problem of low persistence and repeatability. On the other hand, the present invention has made it possible to repeatedly vary the size of the bubble complex provided with a core made of perfluorocarbon and a shell on the outside. For example, after providing the bubble complex provided with a core made of the perfluorocarbon of a liquid phase and a shell made of elastic material on the outside of the core, as shown in FIG. 1, when external stimuli capable of vaporizing the perfluorocarbon (for example, capable of vaporizing the perfluorocarbon by heating the complex or applying ultrasonic waves or lasers to the complex) are applied to the bubble complex, the core expands, and the shell expands as the core expands, thereby causing the bubble to expand so that the complex is increased in size. Subsequently, when the external stimuli are removed in this state, the perfluorocarbon is liquefied again, the core shrinks, and the shell shrinks as the core shrinks so that the bubble complex returns to the original size. Further, as the external stimuli are applied and removed repeatedly, the bubble complex stably repeats a process of increasing and decreasing in size.

The bubble complex according to another embodiment of the present invention includes a core (not shown) made of perfluorocarbon, a coating layer (not shown) encapsulating the core and made of alginate, and a shell (not shown) encapsulating the coating layer and protecting the core by expanding and contracting together when the core expands and contracts. The bubble complex according to the another embodiment of the present invention is the same as the bubble complex according to the first embodiment, except that there is the coating layer between the core and the shell, and thus, only the coating layer, which is a different part, will be described below.

The coating layer is positioned between the core and the shell and is made of alginate. The perfluorocarbon and an elastic material may cause the core to be skewed toward the edge of the bubble complex (that is, a shell having a uniform thickness is not provided on the outside of the core), due to the density difference thereof. Meanwhile, when the shell is provided after the coating layer made of alginate has been provided on the outside of the core, the core may be positioned at the center of the bubble complex. However, the coating layer is provided with a thin thickness (preferably having a thickness of 0.01 to 0.1 mm) so as to be broken in a first expansion process of the core and thus does not affect the repeated size-variation of the bubble complex.

In still another embodiment of the present invention, a method of preparing the bubble complex includes an injection step of injecting perfluorocarbon into an elastic material liquid solution, an obtaining step of obtaining the perfluorocarbon whose outer surface is encapsulated with the elastic material liquid solution by absorbing the perfluorocarbon injected into the elastic material liquid solution, a re-injection step of injecting the perfluorocarbon whose outer surface is encapsulated with the elastic material liquid solution into a supporting liquid solution, and a curing step of providing the bubble complex provided with the core made of the perfluorocarbon and a shell, which encapsulates the core and is made of the elastic material, by rotating a container containing the supporting liquid solution to apply centrifugal force to the supporting liquid solution and simultaneously naturally curing the supporting liquid solution.

The injection step is the step of injecting the perfluorocarbon into the elastic material liquid solution, wherein perfluorocarbon in a state of gas or liquid is injected into the elastic material liquid solution, whereby the bubbles or liquid droplets of the perfluorocarbon are allowed to be positioned in the elastic material liquid solution. Here, a PDMS liquid solution, for example, may be used as the elastic material liquid solution.

The obtaining step is the step of obtaining the perfluorocarbon whose outer surface is encapsulated with the elastic material solution by absorbing the perfluorocarbon injected into the elastic material liquid solution and obtains the perfluorocarbon, whose outer surface is encapsulated with the elastic material liquid solution, by sucking the perfluorocarbon injected into the elastic material liquid solution by using, for example, a micro channel, micro tube, syringe, and the like.

The re-injection step is the step of injecting the perfluorocarbon whose outer surface is encapsulated with the elastic material liquid solution into the supporting liquid solution, wherein the supporting liquid solution has a density similar to the elastic material liquid solution (the supporting liquid solution may have a density less or greater than the elastic material liquid solution within a range of 10%) but has high viscosity (the supporting liquid solution may have a viscosity of two to four times of the elastic material liquid solution). Here, an epoxy resin, for example, may be used as the supporting liquid solution.

The curing step is the step of providing the bubble complex provided with the core made of perfluorocarbon and the shell, which encapsulates the core and is made of the elastic material, by rotating the container containing the supporting liquid solution to apply centrifugal force to the supporting liquid solution and simultaneously naturally curing the supporting liquid solution for 20 to 30 hours (for example, cured at 20 to 30° C.). At this time, the perfluorocarbon and the elastic material may cause the core to be skewed toward the edge of the bubble complex (that is, a shell having a uniform thickness is not provided on the outside of the core), due to the density difference thereof, but when the centrifugal force is applied thereto, the core may be positioned at the center of the bubble complex. However, when centrifugal force is applied, since the perfluorocarbon whose outer surface is encapsulated with the elastic material liquid solution may adhere to a wall surface of the container, a supporting liquid solution having a density similar to the elastic material liquid solution but having a high viscosity is used, whereby perfluorocarbon whose outer surface is encapsulated with the elastic material liquid solution may be allowed to remain at the center of the container. In the case of PDMS, though being heated (no less than 80° C.) for rapid curing, because a phase change is made in a process of curing via heating when perfluorocarbon having a low boiling point is used, the curing occurs at a temperature at which the phase change of perfluorocarbon does not occur in the curing process.

A method of preparing the bubble complex according to still another embodiment of the present invention includes: a first injection step of injecting perfluorocarbon into an alginate liquid solution; a first obtaining step of obtaining perfluorocarbon whose outer surface is encapsulated with the alginate liquid solution by absorbing the perfluorocarbon injected into the alginate liquid solution; a second injection step of injecting the perfluorocarbon whose outer surface is encapsulated with the alginate liquid solution into corn syrup; a second obtaining step of obtaining the perfluorocarbon coated in turn with the alginate liquid solution and the corn syrup by absorbing the perfluorocarbon injected into the corn syrup; a coating step of providing a PFC-coating layer complex, which has the core made of the perfluorocarbon and a coating layer encapsulating the core and made of alginate, the PFC-coating layer complex provided through a reaction that occurs as the alginate liquid solution is brought into contact with a calcium chloride solution as the corn syrup gradually dissolves by injecting the perfluorocarbon coated in turn with the alginate liquid solution and corn syrup into calcium chloride solution to react to each other; a third injection step of injecting the PFC-coating layer complex obtained in the coating step into an elastic material liquid solution; a third obtaining step of obtaining the PFC-coating layer complex whose outer surface is encapsulated with the elastic material liquid solution by absorbing the PFC-coating layer complex injected into the elastic material liquid solution; a fourth injection step of injecting the PFC-coating layer complex whose outer surface is encapsulated with the elastic material liquid solution into a supporting liquid solution; and a curing step of providing the bubble complex provided with the core made of the perfluorocarbon, a coating layer, which encapsulates the core and is made of the alginate, and a shell, which encapsulates the coating layer and is made of the elastic material, and the like. The perfluorocarbon and the elastic material may cause the core to be skewed toward the edge of the bubble complex due to the density difference thereof. Meanwhile, when the shell is provided after the coating layer made of alginate has been provided on the outside of the core, the core may be positioned at the center of the bubble complex. It is important that the coating layer is provided with a thin thickness, so as to be broken in a first expansion process of the core and thus does not affect the repeated size-variation of the bubble complex. To this end, by using the corn syrup, a reaction occurs as the alginate liquid solution is brought into contact with the calcium chloride solution as the corn syrup gradually dissolves, so that the alginate coating layer is provided, thereby allowing a thin coating layer to be provided.

The method of preparing the bubble complex according to still another embodiment of the present invention includes a mold preparation step of preparing a mold provided with a groove having a shape corresponding to the bubble complex, and a curing step of providing the bubble complex provided with a core made of perfluorocarbon and a shell, which encapsulates the core and is made of elastic material, by naturally curing after pouring elastic material solution into the groove, then injecting the perfluorocarbon into the solution.

Hereinafter, the present invention will be described in more detail through embodiments. However, these are only for explaining the present invention in more detail, and the scope of the present invention is not limited thereto.

<Embodiment 1> Preparation of a Bubble Complex

1. Liquid droplets, having a diameter of approximately three mm, of PFC (perfluorohexane (density was 1.68 g/ml) was used) were injected into a PDMS liquid solution (density was 1.03 g/ml, and viscosity was 3900 cps). Then, provided the liquid droplets of the PFC were sucked using a syringe and injected into epoxy resin (density was 1.10 g/ml, and viscosity was 10000 cps) positioned in the container, the PFC whose outer surface was encapsulated with the PDMS liquid solution was positioned in the epoxy resin. Subsequently, by allowing the PDMS to be cured by rotating and keeping the container at room temperature for 24 hours, the bubble complex (perfluorocarbon complex), which was provided with a core made of the PFC and a shell encapsulating the core and made of PDMS, was provided.

2. The liquid droplets of PFC (perfluorohexane was used) were injected into the alginate liquid solution. Then the liquid droplets of the PFC were sucked using a syringe and were injected into the corn syrup. Again, the liquid droplets of the PFC were sucked using a syringe and then were injected into a calcium chloride solution to react to each other. At this time, a reaction occurred as the alginate liquid solution was brought into contact with the calcium chloride solution as the corn syrup gradually dissolved in the liquid droplets of the PFC coated in turn with the alginate liquid solution and the corn syrup. As a result, a PFC-coating layer complex, which had the core made of perfluorocarbon and a coating layer encapsulating the core and made of alginate, was provided. Subsequently, by applying other conditions being the same as 1 of embodiment 1, except that the PFC-coating layer complex was used instead of liquid droplets of the PFC, the bubble complex (perfluorocarbon complex) provided with the core made of the perfluorocarbon, a coating layer, encapsulating the core and made of the alginate, and a shell, encapsulating the coating layer and made of the elastic material, was provided. Here, the alginate liquid solution was provided by mixing two g of sodium alginate per 100 ml of distilled water, and the calcium chloride solution was provided by mixing one g of calcium chloride per 100 ml of distilled water.

3. By applying other conditions being the same as 1 of embodiment 1, except that the liquid droplets, having a diameter of approximately one mm, of PFC (perfluorohexane was used) were used and that a PDMS liquid solution, which was provided by mixing a base of Sylgard-186, a base of Sylgard-184, curing agent of Sylgard-186, and curing agent of Sylgard-184 in a weight ratio of 3:7:0.3:0.7, was used, the bubble complex (perfluorocarbon complex) provided with the core made of the PFC and a shell, encapsulating the core and made of PDMS, was provided.

4. A rod-shaped bubble complex (perfluorocarbon complex) provided with the core made of PFC and a shell, encapsulating the core and made of PDMS, was provided by preparing a polycarbonate substrate provided with a groove having a diameter of 7.5 mm and a height of 5 mm, pouring the PDMS liquid solution up to 2 mm in the groove to cure, and then pouring the PDMS liquid solution and liquid droplets of PFC sequentially to cure. Here, the PDMS liquid solution was provided by mixing a base of Sylgard-186, a base of Sylgard-184, and curing agent of Sylgard-184 in a weight ratio of 3:7:0.4.

5. A micro-bullet provided with the bubble complex (perfluorocarbon complex), having a core and a shell positioned inside an outer wall, was provided, by injecting the PDMS liquid solution into a mold to cure, then providing the outer wall of the bullet by a casting method, and then subsequently pouring the PDMS liquid solution and liquid droplets of the PFC inside the outer wall to cure. Here, for the PDMS liquid solution, the PDMS liquid solution used in 4 of embodiment 1 was used.

<Embodiment 2> Confirmation of a Size and Shape of a Bubble Complex

Figure 2:
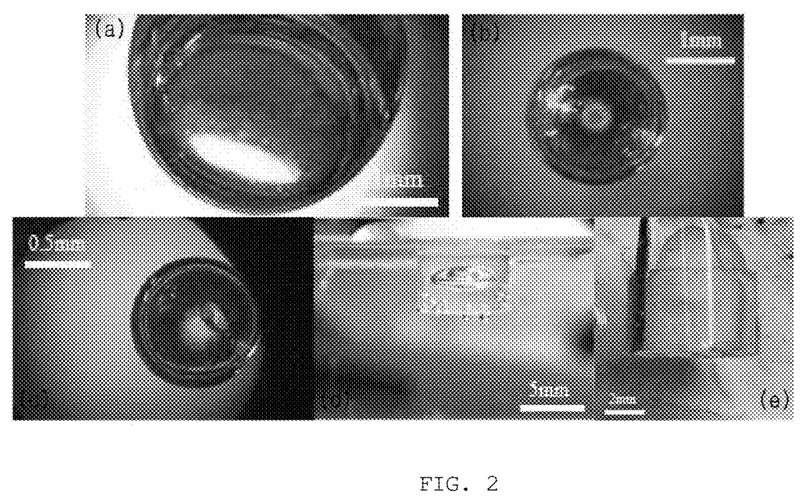
FIG. 2 is a view illustrating digital microscope images of the bubble complex according to the embodiment of the present invention.

1. Each of the bubble complex prepared in embodiment 1 was measured in a digital microscope and shown in FIG. 2. FIG. 2(a) is an image of the bubble complex prepared in 1 of embodiment 1, FIG. 2(b) is an image of the bubble complex prepared in 2 of embodiment 1, FIG. 2(c) is an image of the bubble complex prepared in 3 of embodiment 1, FIG. 2(d) is an image of the bubble complex prepared in 4 of embodiment 1, and FIG. 2(e) is an image of the bubble complex prepared in 5 of embodiment 1.

2. Looking at FIG. 2, it may be seen that: the bubble complex prepared in 1 of embodiment 1 is a spherical shape having a core having a diameter of 3 mm and a shell having a thickness of 0.3 mm; the bubble complex prepared in 2 of embodiment 1 is a spherical shape having a core having a diameter of 2 mm, a coating layer having a thickness of 0.09 mm, and a shell having a thickness of 0.06 mm; the bubble complex prepared in 3 of embodiment 1 is a spherical shape having a core having a diameter of 1 mm and a shell having a thickness of 0.05 mm; the bubble complex prepared in 4 of embodiment 1 is a rod shape having a diameter of 7.5 mm and a height of 5 mm with a core provided inside the shell; and the micro-bullet prepared in 5 of embodiment 1 has the rod-shaped bubble complex having a shell, having a height of 4.5 mm and encapsulating a core, is positioned inside the outer wall.

Figure 3:
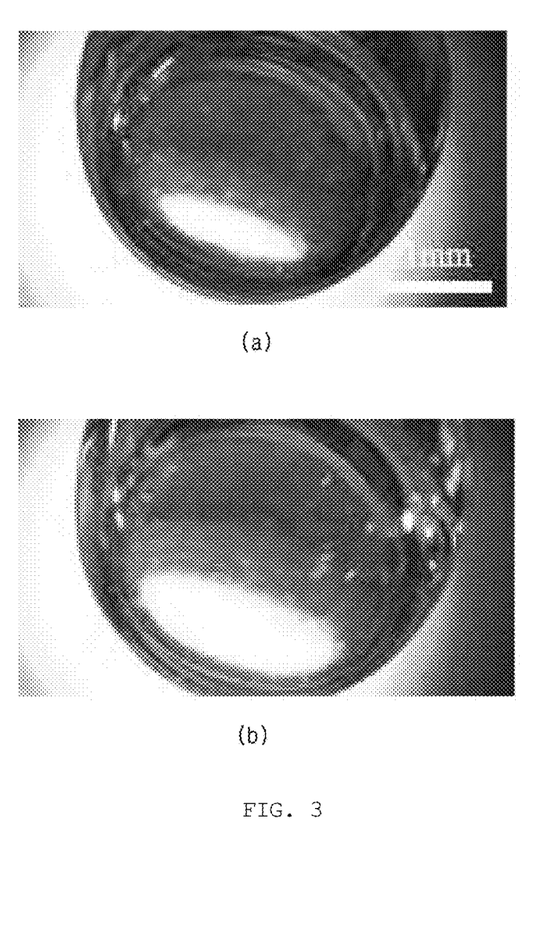
FIGS. 3, 4, and 5 are views illustrating digital microscope images for confirming the size-variation of the bubble complex according to the embodiment of the present invention.

<Embodiment 3> Confirmation of Repeated Size-Variation of a Bubble Complex Against External Stimuli 1. To confirm the repeated size-variation of the bubble complex against the external stimuli, water of 70° C., above a boiling point (59° C.) of PFH, was poured into a water tank to be full, a glass slide of a glass material having high thermal conductivity was put on top of the water tank, and each of the bubble complexes prepared in 1 and 3 of embodiment 1 was placed on a top surface of the slide glass, so that heat energy was allowed to be sufficiently transferred to a core (heating process). When the bubble complex was sufficiently expanded due to temperature change, a liquefaction phenomenon of the core and a contraction phenomenon of the shell were induced in a manner of subtracting hot water from the water tank and adding cold water of 20° C. (cooling process). After repeatedly exchanging the water of 70° C. and the water of 20° C. (that is, repeatedly performing heating and cooling), the bubble complex was measured with a digital microscope, whereby iterative size-variation of the bubble complex was confirmed. FIG. 3 is a view illustrating digital microscope images, the image before the heating process in FIG. 3(a) and the image after the heating process in FIG. 3(b), having measured the bubble complex prepared in 1 of embodiment 1.

Figure 4:
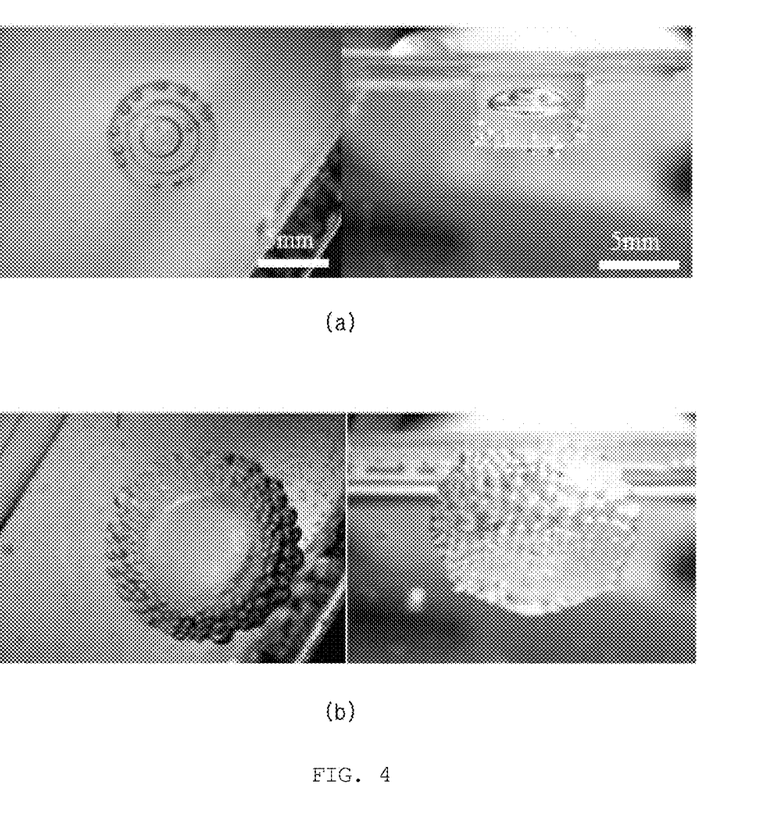
Figure 5:
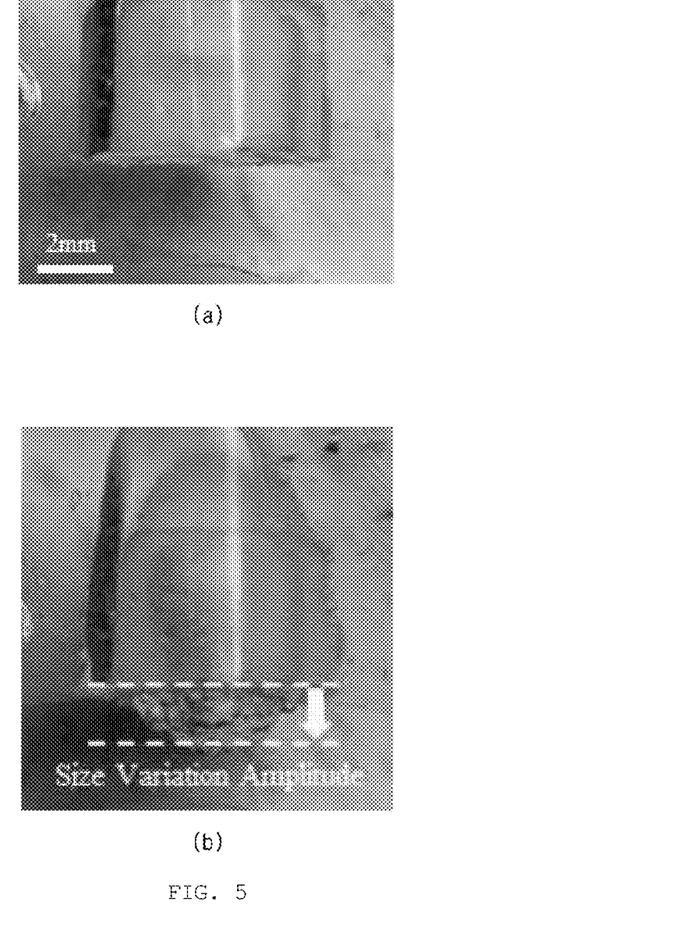

2. Experiments were performed by applying other conditions being the same as 1 of embodiment 3, except that the bubble complex prepared in 4 of embodiment 1 and the micro-bullet prepared in 5 of embodiment 1 were put in the water instead of the top surface of the slide glass. FIG. 4 is a view illustrating digital microscope images, the image before the heating process in FIG. 4(a) and the image after the heating process in FIG. 4(b) having measured the bubble complex prepared in 4 of embodiment 1, and FIG. 5 is a view illustrating digital microscope images, the image before the heating process in FIG. 5(a), and the image after the heating process in FIG. 5(b) having measured the micro-bullet prepared in 5 of embodiment 1.

3. Looking at experimental results for the confirmation of the repeated size-variation of the bubble complex against external stimuli, the bubble complex prepared in 1 of embodiment 1 was not damaged even after heating and cooling 6 cycles (here, the water of 100° C. was used in 4th to 6th heating processes), the diameter increased (up to 8% increase) in the heating process, and the diameter was restored to a level the same as before performing the experiment in the cooling process. In the case of the bubble complex prepared in 3 of embodiment 1, the diameter increased to 2.72 mm in the heating process, and the diameter was reduced down to 1.83 mm in the cooling process, and in the case of the bubble complex prepared in 4 of embodiment 1, no damage occurred until heating and cooling were performed 12 cycles, so that no PFC leaked, the length increased (the diameter increased up to 56%, the length increased up to 66%) in the heating process, and the diameter and length were restored to the level the same as before performing the experiment in the cooling process. In the case of the micro-bullet prepared in 5 of embodiment 1, no damage occurred even after heating and cooling 8 cycles, so that no PFC leaked, the length of the bubble complex inside the outer wall increased (up to 41% increase) in the heating process, and the length of the bubble complex inside the outer wall was restored to the level the same as before performing the experiment in the cooling process. Therefore, it may be seen that even when external stimuli are applied to the bubble complex to cause a phase change of the core, a shape of the core is maintained by a shell having elastic force, so that the bubble complex having a repeated size-varying may be prepared.

In the above, the applicant has described the exemplary embodiments of the present invention, but these embodiments are only for implementing the technical concept of the present invention and any modification or modification of the present invention should be interpreted as belonging to the scope of the present invention as long as the technical spirit of the present invention is realized.

What is claimed is:

1. A preparing method of a bubble complex, the method comprising:
   injecting perfluorocarbon of a liquid phase into an elastic material liquid solution;
   obtaining the perfluorocarbon whose outer surface is encapsulated with the elastic material liquid solution by absorbing the perfluorocarbon injected into the elastic material liquid solution;
   re-injecting by injecting the perfluorocarbon whose outer surface is encapsulated with the elastic material liquid solution into a supporting liquid solution; and curing the bubble complex provided with the core made of the perfluorocarbon and a shell encapsulating the core and made of an elastic material by rotating a container containing the supporting liquid solution to apply centrifugal force to the supporting liquid solution, and simultaneously naturally curing the supporting liquid solution, wherein a PDMS liquid solution is used as the elastic material liquid solution, and the supporting liquid solution is epoxy resin having a density less or greater than the elastic material liquid solution within a range of 10%, and a viscosity of two to four times of the elastic material liquid solution.

2. The method of claim 1, wherein the supporting liquid solution has a density similar to the elastic material liquid solution but has high viscosity and is cured for 20 to 30 hours at a temperature of 20 to 30° C.

\* \* \* \* \*